United States Patent [19]  
Ichimura

[11] 4,269,941  
[45] May 26, 1981

[54] METHOD FOR ENZYME IMMOBILIZATION
[75] Inventor: Kunihiro Ichimura, Yokohama, Japan
[73] Assignees: Agency of Industrial Science and Technology; Ministry of International Trade & Industry, both of Tokyo, Japan
[21] Appl. No.: 62,486
[22] Filed: Jul. 31, 1979
[30] Foreign Application Priority Data Aug. 9, 1978 [JP] Japan .................................. 53/96804

[51] Int. Cl.$^3$ ............................................. C12N 11/04
[52] U.S. Cl. .................................... 435/182; 435/180
[58] Field of Search ............... 435/174, 177, 180, 181, 435/182

[56] References Cited
U.S. PATENT DOCUMENTS

| 3,959,078 | 5/1976 | Guire | 435/181 X |
| 4,160,698 | 7/1979 | Miyairi et al. | 435/180 X |

OTHER PUBLICATIONS

Ichimura et al., Immobilization of Enzymes with Use of Photosensitive Polymers Bearing Stilbazolium Groups, Chem. Abstr., vol. 90: 68499h, 2/1979 (p. 205), Chem. Lett., vol. 11, 1978 (pp. 1289-1292).
Samokhim et al., Photochemical Immobilization of Enzymes, Chem. Abstr., vol. 90: 2435c, 1/1979 (p. 245).

Primary Examiner—David M. Naff  
Attorney, Agent, or Firm—Oblon, Fisher, Spivak, McClelland & Maier

[57] ABSTRACT

Enzymes are immobilized by dissolving in water a photo-crosslinking resin containing stilbazolium groups, vinyl alcohol units and vinyl acetate units, adding an enzyme to the resultant aqueous solution and exposing the enzyme-containing resin solution to light to induce a crosslinking reaction of the photo-crosslinking resin and produce a polymer containing the enzyme entrapped therein.

8 Claims, No Drawings

METHOD FOR ENZYME IMMOBILIZATION

BACKGROUND OF THE INVENTION

This invention relates to a method for the immobilization of an enzyme by use of a water-soluble photo-crosslinking resin of high sensitivity. Because they do little to cause environmental pollution, water-soluble photosensitive resins are used as photoresists and photo-milling agents. In recent years, the potentiality of their adoption for the immobilization of bio-active materials such as enzymes has come to attract increasing attention.

The methods heretofore proposed to the art for the purpose of immobilization of enzymes are broadly divided into three types; the type involving the binding of enzymes with carriers, the type involving the crosslinking between enzyme molecules and the type involving the entrapment of enzymes.

Of these methods, the carrier-binding methods accomplish the immobilization of a given enzyme by causing the enzyme to be chemically or physically bound to a suitable carrier. By the manner of binding involved, the methods of this type are sub-divided into a covalent binding method, an ionic binding method, a physical absorption method, etc. These methods, however, have a common disadvantage that in most cases, the steric structure of the enzyme under treatment particularly near the center of activity and the state of the enzyme's electric charge are affected and, consequently, the enzyme's activity is degraded. In immobilizing a particular enzyme, therefore, it has been necessary to examine all the methods and select the optimum method by the principle of trial and error.

The crosslinking methods generally accomplish the required immobilization of a given enzyme by causing the individual enzyme molecules to be covalently bound with one another and, therefore, have an inevitable consequence that the immobilized enzyme exhibits considerably degraded activity compared with the enzyme in its unimmobilized state.

The methods of the type involving the entrapment of a given enzyme are sub-divided into a method which entraps the enzyme in a high-molecular matrix and a method which seals the enzyme in micro-capsules. These methods are capable of immobilizing given enzymes without impairing the molecular structures of the enzymes and, therefore, are attracting attention as highly promising techniques. Particularly the method which entraps the enzyme in a high-molecular matrix is especially noteworth because it can confine the enzyme molecules within the molecules of the high-molecular matrix in much the same way as animals are locked up in cages and, thus, accomplish the immobilization of the enzyme without spoiling the function inherent in the enzyme or impeding a given substrate from obtaining access to the entrapped enzyme.

The methods of the type involving the entrapment of enzymes in high-molecular matrices which have heretofore been proposed to the art include a method which causes a water-soluble high-molecular compound to be thermally crosslinked, a method which causes a water-soluble high-molecular compound to be crosslinked by exposure to radiant rays, a method which causes a vinyl monomer or oligomer to be radically polymerized (G. P. Hicks and S. J. Updike; Anal. Chem., 38, 726, 1966), a method which causes a similar vinyl monomer or oligomer to be photopolymerized (S. Fukui et al; FEBS LETTERS, Vol. 66, No. 2, p. 179 July, 1976) and a method which causes a water-soluble high-molecular compound to be photo-crosslinked through the agency of bis-azide (U.S. Pat. No. 4,160,698), for example.

Of these conventional methods, those methods which accomplish the crosslinking of high-molecular compounds through the agency of thermal or radiant energy have a possibility of causing the deactivation due to the chemical change in the enzyme molecules under treatment and the two methods involving the exposure of matrix compounds to light inevitably use for the purpose of crosslinking reaction those free radicals and nitrene which are highly reactive and therefore devoid of selectivity and, as the result, fall to have enzymes entrapped perfectly intact.

An object of this invention is to provide a method for the immobilization of an enzyme, which method permits the enzyme to be stably entrapped within a matrix of a photosensitive resin while minimizing the possibility of depriving the enzyme of its activity, wherein the enzyme consequently immobilized in the matrix without impairment of its enzymatic function is allowed to react effectively upon a substrate.

SUMMARY OF THE INVENTION

To accomplish the object described above according to the present invention, there is provided a method for the immobilization of an enzyme, which comprises the steps of dissolving in water a photo-crosslinking resin consisting of 0.1 to 10.0 mol% of a unit containing a crosslinking group of the generic formula:

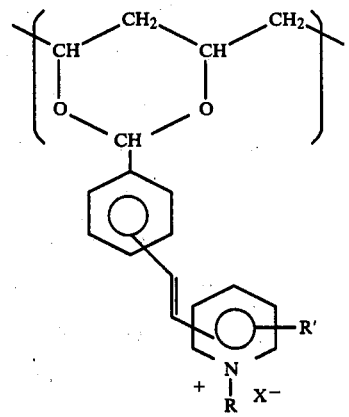

wherein, R represents a hydrogen atom, an alkyl group, a hydroxyalkyl group or an aralkyl group, R' represents a hydrogen atom or alkyl group and X-represents a strongly acidic anion, 70.0 to 99.0 mol% of a unit containing a hydroxyl group of the formula:

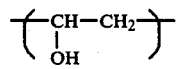

and 0.1 to 30.0 mol% of a unit containing an acetyl group of the formula:

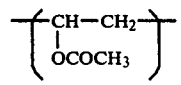

adding the enzyme to the resultant aqueous solution containing the photo-crosslinking resin, and exposing the enzyme-containing resin to light.

In spite of the low concentration of the photo-crosslinking group incorporated, the photo-crosslinking resin obtained by the present invention has high sensitivity and causes a crosslinking reaction upon exposure to light of a wavelength zone unabsorbable by the enzyme. When the enzyme-containing resin is exposed to this light, the enzyme is not inactivated by the radiant energy involved.

Since the amount of the photo-crosslinking group incorporated into the resin is small, the effect which the photo-crosslinking group exerts upon the enzyme is very slight and the cost of the resin itself is low.

DESCRIPTION OF PREFERRED EMBODIMENTS

The inventor carried out a study on a great variety of water-soluble high molecular compounds suitable for the purpose of entrapping enzymes. He further continued a concentrated study with a view to developing a water-soluble photosensitive resin which not only enables a given enzyme to be entrapped in an unimpaired state but also exhibits stably an outstanding entrapping power. The invention has consequently ascertained that a photosensitive resin possessing a hydroxyl group-containing unit and an acetyl group-containing unit in addition to a crosslinking until containing a stilbazolium group satisfies the purpose described above. The present invention has been accomplished on the basis of this knowledge.

To be specific, the present invention effects the immobilization of an enzyme by adding this enzyme to the aqueous solution of a specific photo-crosslinking resin and exposing the resultant enzyme-containing resin to light, which photo-crosslinking resin consists of a crosslinking group-containing unit represented by the generic formula (I):

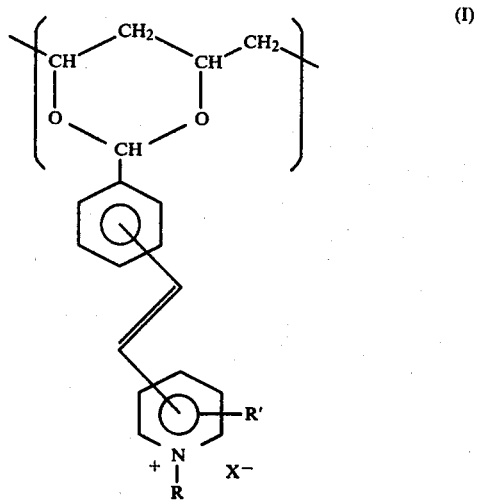

(wherein, R represents a hydrogen atom, an alkyl group, a hydroxyalkyl group or aralkyl group, R' represents a hydrogen atom or alkyl group and X- represents a strong-acid anion such as halogen ion, a sulfate ion or a phosphate ion), a hydroxyl group-containing unit represented by the formula (II):

and an acetyl group-containing unit represented by the formula (III):

in the proportions of 0.1 to 10 mol% of the crosslinking group-containing unit (I), 70 to 99 mol% of the hydroxyl group-containing unit (II) and 0.1 to 30 mol% of the acetyl group-containing unit (III). In consequence of the exposure of the resin to the light, the crosslinking group-containing unit in the resin induces a photo-crosslinking reaction as indicated by the following formula.

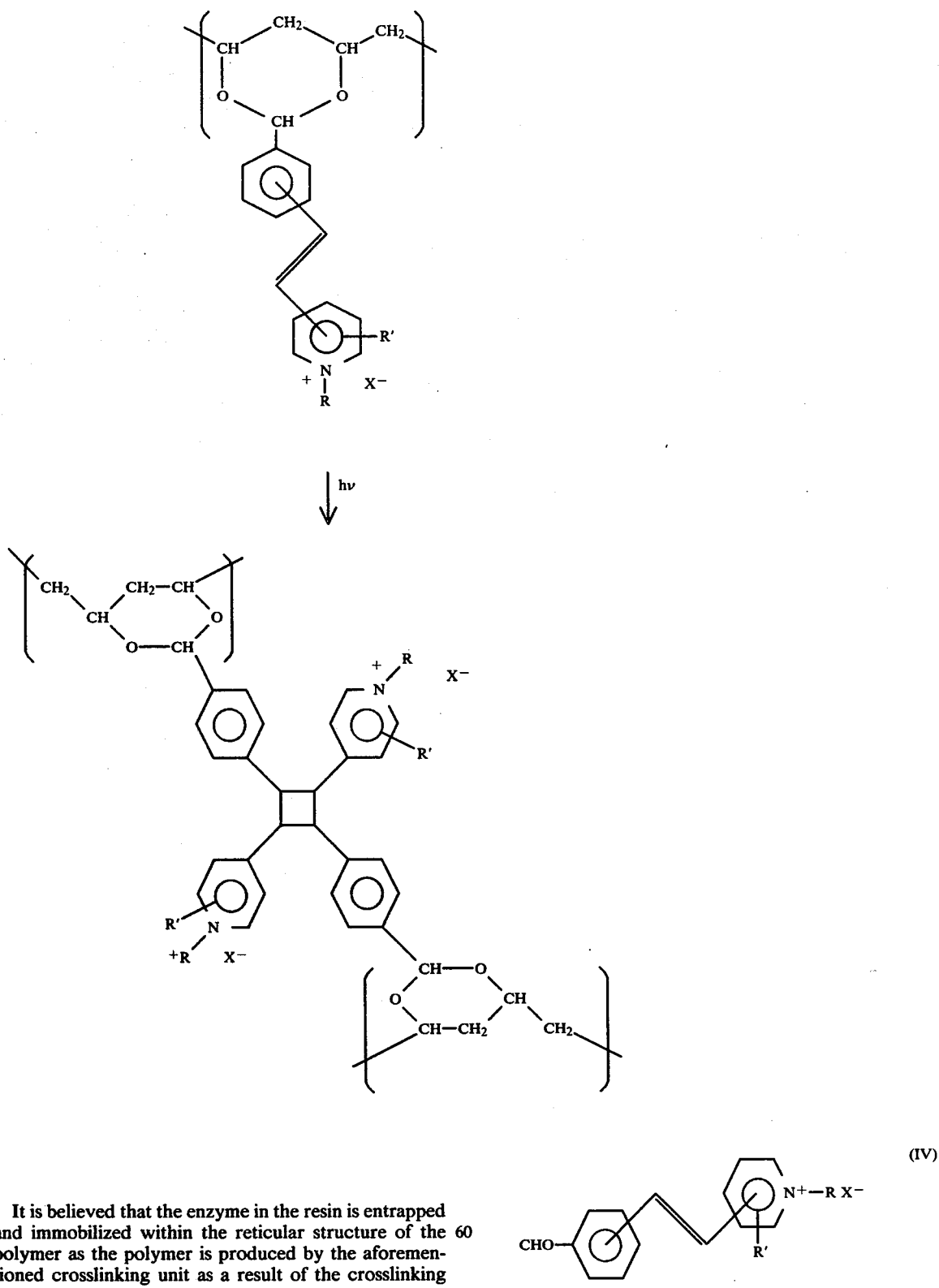

It is believed that the enzyme in the resin is entrapped and immobilized within the reticular structure of the polymer as the polymer is produced by the aforementioned crosslinking unit as a result of the crosslinking reaction.

The photo-crosslinking resin to be used in the present invention can be produced by causing a partially unsaponified polyvinyl alcohol containing an acetyl group to react upon a formylstilbazolium salt represented by the generic formula (IV):

(wherein, R, R' and X⁻ have the same meaning as defined above) through the catalysis with an acid.

the stilbazolium salts of the generic formula (IV) which are usable for this invention include hydrochlorides, hydrobromides, hydroiodides, perchlorates, methosulfates, methane sulfonates and p-toluene sulfonates of N-methyl-α-(p-formylstyryl)-pyridinium, N-methyl-γ-(p-formylstyryl)-pyridinium, N-methyl-α-(m-formylstyryl)-pyridinium, N-allyl-α-(p-formylstyryl)-pyridinium and N-allyl-γ-(p-formylstyryl)-pyridinium, for example.

These stilbazolium salts can be produced by subjecting the corresponding picolines or N-alkylpicolinium salts to a poly-condensation reaction with a formylbenzaldehyde such as terephthal dialdehyde or isophthal dialdehyde.

The content of the crosslinking group-containing unit represented by the aforementioned formula (I) in this photo-crosslinking resin is required to fall in the range of from 0.1 to 10 mol% based on the whole amount of the resin. When it is less than the lower limit, the photo-crosslinking reaction proceeds insufficiently even though the resin is irradiated with light. When it exceeds the upper limit, the unit causes the resin to be gelled.

Addition of the hydroxyl group-containing unit aims at causing the photo-crosslinking resin to be soluble in water. To attain this object, the content of this unit is required to be more than 70 mol% based on the whole amount of the resin. When it is less than 70 mol%, the resin exhibits poor solubility in water of any temperature.

The acetyl group-containing unit added to the photo-crosslinking resin functions to control the solubility of polyvinyl alcohol in water. When the content of this unit in the resin is too large, the solubility becomes poor. The upper limit of the content for obtaining desired solubility is 30 mol% based on the whole amount of the resin.

The aforementioned high-molecular acetalization reaction can be effectively carried out through the catalysis with an acid. If, in this reaction, the acid as the catalyst is used in an excess amount, the amount of the anion ($X^-$) contained in the produced resin will proportionally increase. In this high-molecular acetalization reaction, the time required for completion of the reaction can be reduced by applying heat to the reaction system or by increasing the amount of the acid as the catalyst. In this reaction, the portions of stilbazolium salt and acid remaining in their unaltered forms after the reaction are desired to be removed as thoroughly from the reaction mixture as possible. For this purpose, the resin precipitating in the reaction mixture is repeatedly washed with or precipitated in alcohol. Generally, thorough removal of the unaltered reactants can be obtained by subjecting to one cycle of reprecipitation the resin which has been repeatedly washed with alcohol.

The photo-crosslinking resin obtained as described above is desired to have a polymerization degree in the range of from about 300 to about 4000. In spite of the fact that the concentration of the photosensitive group, namely the stilbazolium group, incorporated in this photo-crosslinking resin is as low as to fall in the range of from 0.1 to 10 mol%, the photo-crosslinking resin exhibits a high degree of photosensitivity without necessitating use of any extra sensitizer, with the aforementioned polymerization degree as a possible contributory factor. When the immobilization of an enzyme is effected by use of this photo-crosslinking resin, therefore, the possible effect brought about by the photo-crosslinking group upon the enzyme can be minimized. When the polymerization degree of the resin is 1700 and the concentration of the photo-crosslinking group incorporated in the resin is only 1 mol%, for example, the photosensitivity of this resin is as high as 12 times that of the polyvinyl cinnamate sensitized with 5-nitroacenaphthene. When the concentration of the incorporated photo-crosslinking group is increased to 1.4 and 1.9 mol%, the photosensitivity of the produced resin reaches the levels about 30 times and about 80 times the sensitivity of the aforementioned sensitized polyvinyl cinnamate.

The photo-crosslinking resin of this invention is insolubilized by light of a wavelength zone exceeding 300 nm, namely the wavelength zone absolutely unabsorbable by the enzyme under treatment. Thus, the otherwise possible inactivation of the enzyme by the exposure to the light can be avoided where the immobilization of the enzyme is made by this photo-crosslinking resin. It has been demonstrated through experiments that the hydrophilic amino acid residues which abundantly occur on the surface of the enzyme molecules take absolutely no part in the dimerization reaction of stilbazolium groups indispensable to the photo-insolubilization mentioned above. The photo-crosslinking resin of this invention, accordingly, enjoys an advantage that its capacity for the photo-insolubilization is degraded very little even in the presence of the enzyme.

Since use of this resin permits the required immobilization of a given enzyme to be carried out in normal atmosphere, the immobilization proves to be an easy operation of high reproducibility. Further in this resin, the number of regions capable of affecting the electrostatic condition of the enzyme is extremely small so that the possible effect of these regions can be minimized. On the other hand, the required concentration of the photosensitive group in the resin is small. Owing to all these factors, the cost of the resin of this invention is low.

Now, the method to be used for the immobilization of a given enzyme by use of the photo-crosslinking resin of this invention will be described.

First, the photo-crosslinking resin is dissolved in water to a concentration of about 1 to 40% by weight. In this case, the dissolution of the resin in water is accelerated by application of heat. Then, the enzyme in a prescribed amount is added, either by itself or in the form of an aqueous solution, to the resultant aqueous solution of the resin and properly treated to produce a homogeneous solution. The concentration of the enzyme in the solution is generally in the range of from about 0.1 to 20% by weight, although it is variable to some extent with the application for which the immobilized enzyme is intended or the particular kind of the enzyme to be actually used.

Subsequently, the enzyme-containing solution is exposed to light to induce a crosslinking reaction of the photo-crosslinking resin and immobilize the enzyme. In this case, it is more advantageous to use this solution in the form of a film than otherwise. The solution can be converted into a gelatinous, water-insoluble film by causing the solution to be spread spontaneously on or applied manually to a smooth surface such as of a glass plate and exposing the deposited layer of the solution to the light from which the ultraviolet ray has been screened off. As occasion demands, the solution deposited on the smooth surface as described above may be dried in air before it is exposed to the light. By the latter procedure, there is obtained a transparent, strong film, depending somewhat upon the length of the exposure time, the concentration of the photo-crosslinking group and the polymerization degree of the resin. The spreading or applying of the solution on the smooth surface may be carried out in the presence of a three-dimensional reinforcing carrier such as of gauze, filter paper or threads. The use of such a reinforcing carrier permits the film to be produced in desired shape and size. Again in this case, a gelatinous film deposited fast on the three-dimensional reinforcing carrier can be obtained by coating the carrier with the solution and immediately exposing the coated carrier to the light. When the coated carrier is dried in air before it is exposed to the light, there is obtained a strong film of high wettability.

It is generally preferable to perform the operations described above in a dark room. Since the resin of this invention exhibits notably diminished photosensitivity to yellow light, however, the operations may be effectively carried out under a yellow light.

The sources of light for the exposure of the enzyme which are advantageously usable for the immobilization of an enzyme by the method described above include a xenon arc lamp, a fluorescent lamp, a high-pressure mercury lamp as well as solar rays. Although the length of the exposure time is variable with the nature, size and water content of the photo-crosslinking resin involved, it is generally in the range of from 5 seconds to 30 minutes when the film has been dried in air before the exposure or in the range of from one to 30 minutes when the film is still in the form of an aqueous solution at the time of the exposure. Although the exposure time selected in the low-value portion of the specified range suffices for the purpose of immobilization, the light used for the exposure is desired to be treated so as to be freed from the portion of light absorbable by proteins, namely the light of a wavelength zone not exceeding about 320 nm. This elimination of the unwanted portion of light can be attained by use of a glass plate, for example. Where the enzyme-containing aqueous solution is in the form of a film, the exposure effected on one side of the film is generally found sufficient. Where the film of the same aqueous solution incorporates a reinforcing carrier such as of filter paper or possesses a large wall thickness, the exposure is desired to be effected on both sides of the film.

The enzymes to which the method of the present invention is applicable are not specifically limited. Examples of enzymes for which the present invention is applicable include catalases as well as invertases, glucoamylases, urease and trypsin. A compound enzyme film may be prepared by mixing two or more such enzymes and having them simultaneously immobilized.

Upon contact with added water, the immobilized enzyme composite film obtained by the method of this invention is readily swelled and rendered more permeable to a given substrate. Since the enzyme can be incorporated in a concentration of as high as 20% by weight into the composite, this invention can prepare the immobilized enzyme composite in a state possessing a very high level of activity. Further, the possible inactivation of the enzyme can be repressed to a great extent because the points of crosslinking occur without affecting the enzyme in any way.

The immobilized enzyme prepared by the method of this invention exhibits activity approximately equalling 30 to 90% of the activity which the enzyme exhibits in its untrapped state prior to the immobilization. The lowered activity obtained after the immobilization is about 40% in the case of invertases, about 86% in the case of glucoamylases and about 30% in the case of catalases.

Since the immobilized enzyme composite obtained as described above is generally in the form of a film, it may be chopped into small flakes, which are mixed with a given substrate for batchwise treatment or placed in a column for continuous treatment involving the passage of the substrate through the packed column. Alternatively, the immobilized enzyme composite may be used in its original form of a film by a method which involves the passage of a given substrate through the film. Thus, this immobilized enzyme composite is suitable for special use such as in enzymatic electrodes as well as for ordinary use in enzymatic reactions.

By the method of this invention, immobilized enzyme composites suitable for the various uses described above can be produced easily in a large quantity.

Now, the present invention will be described in further detail below by reference to examples.

EXAMPLE 1

In 20 ml of ethanol, 5.00 g of N-methyl-α-picolinium-p-toluene sulfonate and 10.0 g of terephthal dialdehyde were dissolved hot. The resultant mixture, after addition thereto of five drops of piperidine, was refluxed for three hours. The hot solution was cooled and then freed from about 10 ml of the ethanol by distillation under vacuum. It was mixed with ethyl acetate to produce a yellow precipitate. The yellow precipitate was separated by decantation and washed twice with ethyl acetate. When the precipitate was dissolved in hot ethanol and ethyl acetate was gradually added to the solution, bright yellow crystals were educed. These crystals were collected by filtration, washed with ethyl acetate and dried to afford 5.57 g of N-methyl-α-(p-formylstyryl)-pyridinium-p-toluene sulfonate.

Then, in 200 ml of hot water, 15 g of 87% saponified polyvinyl alcohol having a polymerization degree of 1700 was dissolved and, thereafter, 3.5 g of N-methyl-α-(p-formylstyryl)-pyridinium-p-toluene sulfonate was dissolved. The solution was stirred with 8.0 g of 85% phosphoric acid added thereto at 65° C. for 14 hours. The resultant reaction solution was poured in a fine thread into 2 liters of acetone and then stirred in the acetone. The precipitate which was consequently formed was separated by decantation and washed three times with methanol. The precipitate was again dissolved in 200 ml of hot water and the resultant solution was poured into 2 liters of acetone. The precipitate which consequently occurred was separated and then washed once with methanol and dried. Consequently, there was obtained 14.8 g of a photo-crosslinking resin consisting of 1.7 mol% of a crosslinking group-containing unit, 85.3 mol% of a hydroxyl group-containing unit and 13.0 mol% of an acetyl group-containing unit. This resin exhibited a relative sensitivity 9 times that of a sensitized polyvinyl cinnamate.

In 8 ml of distilled water, 500 mg of the aforementioned photo-crosslinking resin was dissolved and 70 ml of a catalase solution (bovine liver, 304,000 units/ml made by Seikagaku Kygyo Co., Ltd.) was added thereto. The resultant solution was applied to a smooth surface glass plate and dried in air for one hour in a dark room. The film consequently formed on the glass plate was exposed to the light from a 450-W high pressure mercury lamp for three minutes and immersed in water. As the result, a transparent film peeled off the glass plate. The catalase in this film exhibited relative activity of 30%. When this film was suspended in a 0.05-M phosphate buffer solution having a pH value of 7.0 and hydrogen peroxide was added to the solution, air bubbles rose violently from the film.

When the liquid in which the film was peeled off the glass plate was similarly mixed with hydrogen peroxide, practically no liberation of oxygen was observed.

The catalase activity in the film was determined by the following procedure. The transparent film was dried overnight under vacuum. A 20-mg sample of the dried film was vigorously stirred in 8 ml of a buffer solution of pH 6.95 with a magnetic stirrer and 0.2 ml of an aqueous 0.5 N hydrogen peroxide solution was added all at once to the stirred system at 25° C. Along the course of time, the amount of oxygen liberated was measured to determine the constant of the reaction velocity involved. This constant was reported as the catalase activity.

EXAMPLE 2

The aqueous solution of the catalse-containing photo-crosslinking resin prepared by following the procedure of Example 1 was applied to a glass plate. The layer thus deposited on the glass plate was immediately exposed to the light from a 450-W mercury lamp for ten minutes. The film consequently formed was thoroughly washed with a phosphate buffer solution of pH 7.00. The washings and the gelled product were tested for activity. When the washings were mixed with 0.5-M hydrogen peroxide, slight liberation of air bubbles was recognized. When the gelled product was mixed with the hydrogen peroxide, however, vigorous liberation of oxygen was observed to occur from the film, indicating presence of catalase activity.

EXAMPLE 3

In 5 ml of distilled water, 500 mg of the photo-cross-linking resin prepared by following the procedure of Example 1 was dissolved. The resultant solution was stirred with 10 mg of glucoamylase (27 units/mg made by Seikagaku Kogyo Co., Ltd.) dissolved in 1 ml of distilled water at room temperature for 20 minutes to produce a homogeneous solution. This solution was applied uniformly to a 150-mesh gauze of Tetlon (polyester fibers made by Teijin Co., Ltd. of Osaka, Japan) of an area of 20×20 cm$^2$ placed on a glass plate and then left to dry in air. The film thus produced was exposed to the light radiated from a 450-W high pressure mercury lamp and filtered so as to screen off the portion of light having a wavelength zone not exceeding 320 nm, with the exposure given for an equal duration to each side of the film. The total exposure time was 4, 30 and 60 minutes respectively in the three runs of test conducted. The film thus exposed to the light was washed with water and peeled off the glass plate, to afford an immobilized enzyme film deposited on the gauze.

The films of immobilized enzyme and their respective washings obtained in the test above were tested for enzymatic activity at 37° C. The results are shown in Table 1. The percentages for the enzyme immobilized to the film and the activity in the washings indicated for the exposure times of 4 and 30 minutes in the table are relative values based on the total activity of the immobilized enzyme and activity in the washings at 60 minutes exposure time taken as 100.

TABLE 1

| Exposure time (min.) | Activity of enzyme immobilization to film (%) | Activity of enzyme in washings (%) | Total of activity (%) |
| --- | --- | --- | --- |
| 4 | 16 | 82 | 98 |
| 30 | 78 | 4 | 82 |
| 60 | 97 | 3 | 100 |

It is learnt from the table that so far as the exposure time exceeds the level of 30 minutes, the enzyme is effectively immobilized in the film without reference to the length of exposure time beyond this level.

The activity of the enzyme in the film, as expressed in terms of the relative value in comparison with the original activity, was about 60% and about 80%, when the activity measurement was made at about 37° C. and 45° C., respectively.

The test of the washings and the resin film for their glucoamylase activity was conducted as follows. The washings were adjusted to pH 4.8 and mixed with 5% maltose as the substrate. The mixture was assayed for the amount of the produced glucose by the glucostat method. In the case of the resin film, the resin deposited on a gauze 2.5×4.0 cm$^2$ in area was weighed. Then it was cut into strips about 5 mm in width, suspended in a buffer solution containing 5% maltose and shaken in the solution to induce a reaction. The resultant solution was assayed for the amount of the produced glucose by the glucostat method.

EXAMPLE 4

In 300 ml of hot water, 15 g of 87% saponified polyvinyl alcohol having a polymerization degree of 1700 was dissolved and then 1.50 g of N-methyl-γ-(p-formyl-styryl)-pyridinium-p-toluene sulfonate was added and dissolved. The resultant solution, after addition thereto of 8.0 g of 85% phosphoric acid, was stirred at 83° C. for 14 hours. The reaction solution consequently obtained was cooled and then poured into 2 liters of acetone. The precipitate which occurred consequently was washed twice with methanol and then dissolved in 200 ml of hot water. The aqueous solution was poured into 2 liters of acetone and the precipitate which formed was separated. This precipitate was washed once again with methanol and dried under vacuum to afford 15.3 g of a photosensitive resin consisting of 0.9 mol% of a cross-linking group-containing unit, 86.1 mol% of a hydroxyl group-containing unit and 13.0 mol% of an acetyl group-containing unit.

The resin thus obtained showed a relative sensitivity 8.5 times the sensitivity of a polyvinyl cinnamate sensitized with 5-nitroacenaphthene.

In 7.5 ml of water, 500 mg of the photosensitive resin was dissolved by heating. The solution was cooled and then mixed with 2 ml of aqueous solution containing 10 mg of glucoamylase and stirred for 20 minutes in a dark room. The resultant resin was applied to a gauze of Tetlon in the same way as in Example 2, dried in air and exposed on both sides to the sunlight for five minutes under a clear June sky. When the composite film was immersed in water, the immobilized enzyme film deposited in the gauze could be peeled off. This film was tested for enzymatic activity by faithfully following the procedure of Example 3. It was found that the film retained about 70% of the original activity of the enzyme.

EXAMPLE 5

In 7 ml of distilled water placed under a yellow lamp, 500 mg of the photosensitive resin prepared by following the procedure of Example 4 was dissolved. The solution was stirred with a solution of 3.5 mg of invertase (made by Seikagaku Kogyo Co., Ltd.) in 1 ml of distilled water at room temperature for 20 minutes. The resultant solution was applied to a 150-mesh gauze of Telton having an area of 15×15 cm$^2$ and then dried in air for 15 minutes. The composite film thus produced was exposed to the sunlight under a clear June sky, with the exposure given for an equal duration of two minutes to each side of the film. The film was immersed in distilled water to complete an immobilized enzyme film. By following the procedure of Example 3, thus film was allowed to react on an aqueous 5% sucrose solution as the substrate and then assayed for the produced glucose by the glucostat method. It was shown to exhibit a relative activity of about 30% with reference to the invertase solution at pH 4.8. This film was shaken overnight at 37° C. in a solution of pH 4.5 and then removed from the solution and sucrose was added to the residual solution to a sucrose concentration of 5% by weight. When the resultant sucrose solution was assayed for invertase activity, neither formation of glucose nor elution of enzyme could be recognized.

EXAMPLE 6

In 2 ml of distilled water, 200 mg of the photosensitive resin prepared by following the procedure of Example 4 was dissolved. The solution was mixed with 0.5 ml of an aqueous solution having 5 mg of invertase dissolved therein, to produce a homogeneous solution. This solution was applied to a smooth-surfaced glass plate. When the deposited layer of the solution was exposed to the light from a 450-W high-pressure mercury lamp for five minutes, it was deprived substantially completely of viscosity and converted into a gel. The gel deposited on the glass plate was placed in a beaker and stirred at room temperature with an aqueous 5% sucrose solution added thereto. By testing the stirred solution for the produced glucose with urine testing paper (Uropaper made by Eiken Chemicals Co., Ltd.) the gel was recognized to possess an enzymatic activity.

EXAMPLE 7

In 2 ml of distilled water, 200 mg of the photosensitive resin prepared by following the procedure of Example 4 was dissolved. The solution was mixed with 1 ml of an aqueous solution having 15 mg of invertase dissolved therein, to produce homogeneous solution. The solution was applied to a sheet of filter paper (No. 2 filter made by Toyo Filter Paper Co., Ltd.) dried in air and then exposed to the light from a 450-W high-pressure mercury lamp, with the exposure given for an equal duration of five minutes to each side of the film. The film-coated filter paper was cut into strips and then tested with the same urine testing paper as in Example 6. Consequently, the filter paper was found to possess invertase activity with respect to sucrose as its substrate.

EXAMPLE 8

In 6 ml of distilled water, 500 mg of the photo-sensitive resin prepared by following the procedure of Example 4 was dissolved. In a dark room, the solution was stirred with 1 ml of an aqueous solution containing 10 mg of glucoamylase for 20 minutes. About 100 mg of the viscous resin solution consequently obtained was applied in a thin layer to a microscope slide glass and immediately exposed to the light from a 450-W high-pressure mercurcy lamp, with the exposure time being 5, 20 and 60 minutes in the three runs of test. The exposed film on the slide glass was immersed in 10 ml of a buffer solution with pH 4.8 and the solution was stirred to expel the un-immobilized portion of enzyme out of the film. The washings were mixed with 500 mg of maltose and the resultant reaction mixture was tested for activity at about 27° C. by the glucostat method. The gel which had been washed was washed once with water and immersed in a buffer solution of pH 4.8 containing 5% by weight of maltose, and the buffer solution was stirred at about 27° C. and, at the same time, tested for enzymatic activity by the glucostat method. Table 2 shows the ratios of relative activity of the immobilized and expelled portions of glucoamylase vs. the lengths of exposure time. It is learnt from the results that the ratio of immobilizations reaches about 90% with an exposure time of about 20 minutes and that any addition to the length of exposure time has no effect upon the ratio of enzymatic activity.

TABLE 2

| Exposure time (min.) | Activity in film (%) | Activity in washings (%) | Total of activity (%) |
|---|---|---|---|
| 5 | 43 | 44 | 87 |
| 20 | 89 | 11 | 100 |
| 60 | 89 | 9 | 98 |

EXAMPLE 9

In 25 ml of methanol, 9.40 g of γ-picoline was dissolved and 12.61 g of dimethyl sulfate was introduced dropwise. After the dropwise introduction of the sulfate, the resultant reactant solution was left to stand at room temperature for one hour. It was then mixed with 40.2 g of terephthal aldehyde and heated. The homogeneous solution formed consequently was refluxed for five hours with 1.4 ml of piperidine added thereto. From the refluxed mixture while still hot, 2.55 g of insoluble crystals of a yellowish orange color were separated by filtration. When the filtrate was mixed with 200 ml of an equivoluminally mixed solvent of ethanol and acetone and then left to stand, there ensued education of bulky yellow crystals. The crystals were separated by filtration, washed with acetone and then dried, to afford 23.04 g of 1-methyl-4-(p-formylstyryl)-piridinium methosulfate.

Then, 50 g of 87% saponified polyvinyl alcohol having a polymerization degree of 1700 was dissolved in 650 ml of distilled water, and 7.5 g of 1-methyl-4-(p-formylstyryl)-pyridinium methosulfate was additionally dissolved. The resultant solution was stirred with 50 g of 85% phosphoric acid at 80° C. for five hours. The reaction solution was poured in a fine thread into about 4 liters of acetone and stirred. The precipitate which consequently occurred was separated and washed twice with methanol and then dispersed in methanol. The methanol washings were neutralized with added aqueous ammonia. The resulting precipitate was dissolved in 650 ml of hot water and the hot aqueous solution was poured into 3 liters of acetone. The precipitate formed in the acetone was separated, washed once with methanol and dried. Consequently, there was obtained 45 g of a photo-crosslinking resin consisting of 1.1 mol% of a photo-crosslinking group-containing unit, 85.9 mol% of a hydroxyl group-containing unit and 13 mol% of an acetyl group-containing unit. This resin showed a relative sensitivity 15 times the sensitivity of a sensitized polyvinyl cinnamate.

In a solution having 7.3 mg of urease (25 units/mg) dissolved in 0.5 ml of distilled water, 7.30 g of an aqueous solution containing 10% by weight of the photo-crosslinking resin described above was gently stirred to produce a homogeneous solution. The solution was applied in a layer of uniform thickness to an acrylic resin plate of smooth surface and then dried in air, to produce a transparent film about 20μ in thickness. This film was peeled off the resin plate and was exposed, for five minutes on each side, to the light from a 450-W high-pressure mercury lamp, giving rise to a water-insoluble transparent film. The film was cut into oblong pieces 1×5 cm² in area and left to stand in an aqueous 3% urea solution as the substrate at pH 7.06 at 37° C. by way of a test for enzymatic activity. The activity was determined by the coloration reaction of sodium hypochlorite upon the ammonia formed in consequence of the enzymatic reaction. This test showed that the immobilized enzyme retained about 32% of the original activity of the enzyme.

The urease immobilized as described above in the resin possessed an unusually high level of thermal resistance. Before the immobilization, this enzyme, when maintained at 70° C. and 75° C. for 15 minutes, was deprived of about 52% and 66% respectively of its original activity. In contrast, the immobilized enzyme was deprived of 25% and 65% of the original activity when it was maintained at 80° C. and 87° C. respectively for 15 minutes, indicating that the immobilization served to raise the enzyme's highest working temperature by more than 10° C.

EXAMPLE 10

A suspension of 0.5 ml of xanthin oxidase (5.07 units/ml, made by Miles Laboratories Co., Ltd.) in 60% ammonium sulfate was dialyzed with cold water for two hours to remove ammonium sulfate. In 0.75 ml of the resultant aqueous solution of enzyme, 2.25 g of an aqueous solution containing 10% by weight of the photo-crosslinking resin of Example 9 was gently stirred. The resultant solution was applied in a layer of uniform thickness to an acrylic resin plate of smooth surface and dried in air, to produce a transparent film 35 μm in thickness. This film was peeled off the resin plate and exposed, for 5 minutes on each side, to the light from a 450-W high-pressure mercury lamp, giving rise to a colorless, transparent film insoluble in water. The film was cut into oblong pieces 1×5 cm² and left to react on 0.05 mM xanthin as the substrate in a 0.05 M phosphate buffer solution of pH 7.5 by way of test for enzymatic activity. The activity was determined on the basis of the increase in the absorbancy at 290 nm of the uric acid formed in consequence of the reaction. The test showed that the film retained about 40% of the original activity of the enzyme.

EXAMPLE 11

By following the procedure of Example 10, a film was pooduced by uniformly mixing 5 g of an aqueous solution containing 10% by weight of the photo-cross-linking resin of Example 9 with 2 ml of a glucose oxidase solution (1000 units/ml, made by Miles Laboratories Co., Ltd.). This film was cut into oblong pieces 1×3 cm² and left to react upon a 3% glucose solution as the substrate in a sodium acetate buffer solution of pH 5.75 by way of a test for enzymatic activity. The activity was determined by measuring the amount of hydrogen peroxide liberated using the colorization reaction of the peroxidase-pyrogallol system. Consequently, the immobilized enzyme in the resin was found to show about 97% of activity.

The film thus obtained was caused to react at room temperature for 10 minutes upon a solution containing 3% of glucose. Fifteen repetitions of this reaction led to no discernible degradation in the activity of the enzyme. The enzyme in the film maintained about 80% of its activity after being subjected to the same reaction fifteen more times.

EXAMPLE 12

By following the procedure of Example 9, a photo-crosslinking resin incorporating 1.41 mol% of stilbazolium group was obtained from 50 g of 87% saponified polyvinyl alcohol having a polymerization degree of 1700, 9.0 g of 1-methyl-4-(p-formylstyryl)-pyridinium methosulfate and 50 g of 85% phosphoric acid. This resin showed 30 times the sensitivity of a sensitized polyvinyl cinnamate. A suspension of 2 ml of L-asparaginase (140 units/mg, made by Sigma) in 50% glycerin was dialyzed with salt water at 0° C. for three hours to remove the glycerin. With 18 g of an aqueous solution containing 8% by weight of the aforementioned photo-crosslinking resin, 4.4 ml of the aqueous solution obtained from the dialysis was homogeneously mixed. The resultant solution was applied to an acrylic resin plate of smooth surface and dried in air to produce a film 20 μm in thickness. This film was exposed, for five minutes on each side, to the light from a 450-W mercury vapor lamp. The film was then cut into oblong pieces 1×5 cm² in area, washed with water and tested for enzymatic activity as described below. The enzyme-incorporated film was shaken to react upon 10 mM L-asparagine as the substrate in a 0.05-M Tris buffer solution of pH 8.60, with the resultant mixture analyzed for the amount of the ammonia produced in consequence of the reaction. The L-asparaginase in the film was found to possess 76% of activity.

EXAMPLE 13

With a solution having 40 mg of invertase dissolved in 1 ml of distilled water, 2 g of an aqueous solution containing 10% by weight of the photo-crosslinking resin of Example 9 was homogeneously mixed. The resultant solution was applied in a uniform thickness to an acrylic resin plate of smooth surface and dried in air to produce a transparent film. This film was exposed, for five minutes on each side, to the light from a 450-W high-pressure mercury lamp, giving rise to a transparent, water-insoluble film. This film was cut into square pieces 1×1 cm², suspended in an aqueous 5% sucrose solution and stirred therein at room temperature. When the solution was tested with a urine testing paper (Uropaper), the film was found to possess invertase activity.

What is claimed is:

1. A method for the immobilization of an enzyme, which comprises:
  dissolving in water a photo-crosslinking resin having a polymerization degree of 300 to 4000, consisting of 0.1 to 10.0 mol% of a unit containing a crosslinking group of the formula:

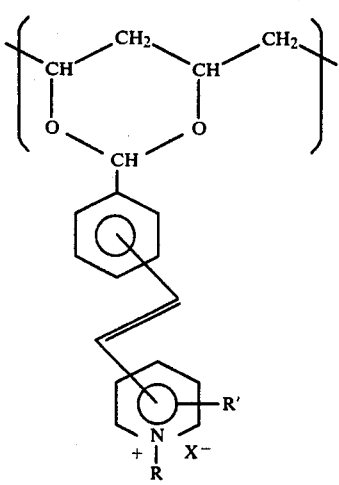

wherein, R represents one member selected from the group consisting of a hydrogen atom, an alkyl group, a hydroxy-alkyl group and an aralkyl group, R' represents one member selected from the group consisting of a hydrogen atom and an alkyl group, and X$^-$ represents a strongly acidic anion, 70.0 to 99.0 mol% of a unit containing a hydroxyl group of the formula:

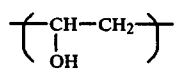

and 0.1 to 30.0 mol% of a unit containing an acetyl group of the formula:

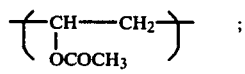

adding the enzyme to the resultant aqueous solution containing the photo-crosslinking resin, and exposing the enzyme-containing resin to light to induce a crosslinking reaction of the photo-crosslinking resin and produce a polymer containing the enzyme entrapped therein, wherein the concentration of the photo-crosslinking resin in water is 1–40% by weight.

2. A method for the immobilization of an enzyme, which comprises dissolving in water a photo-crosslinking resin having a polymerization degree of 300 to 4000, consisting of 0.1 to 10.0 mol% of a unit containing a crosslinking group of the formula:

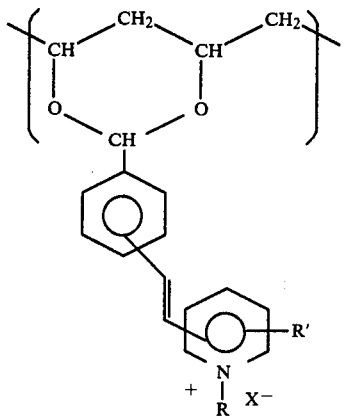

wherein, R represents one member selected from the group consisting of a hydrogen atom, an alkyl group, a hydroxy-alkyl group and an aralkyl group, R' represents one member selected from the group consisting of a hydrogen atom and an alkyl group, and X$^-$ represents a strongly acidic anion, 70.0 to 99.0 mol% of a unit containing a hydroxyl group of the formula:

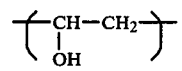

and 0.1 to 30.0 mol% of a unit containing an acetyl group of the formula:

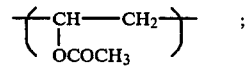

adding an enzyme to the resultant aqueous solution in an amount of from 0.1 to 20% by weight of said solution, and exposing the enzyme-containing resin to light to induce a crosslinking reaction of the photo-crosslinking resin and produce a polymer containing the enzyme entrapped therein; wherein the concentration of the photo-crosslinking resin in water is 1–40% by weight.

3. The method according to claims 1 or 2, wherein ultra-violet rays have been screened off from the light.

4. The method according to claims 1 or 2, wherein the exposure to light is carried out after the enzyme-containing aqueous solution has been caused to flow and spread over a smooth surface.

5. The method according to claims 1 or 2, wherein the exposure to light is carried out after the enzyme-containing aqueous solution has been applied to a smooth surface and allowed to dry in air to form a film.

6. The method according to claims 1 or 2, wherein the exposure to light is carried out after the enzyme-containing aqueous solution has been caused to flow and spread over a reinforcing material.

7. The method according to claim 6, wherein the exposure to light is carried out after the enzyme-containing aqueous solution spread over the reinforcing material has been caused to dry in air to form a film.

8. The method according to claim 7, wherein the reinforcing material is a sheet of gauze made of a synthetic resin.

* * * * *